United States Patent
Hwang et al.

(10) Patent No.: US 9,934,363 B1
(45) Date of Patent: Apr. 3, 2018

(54) AUTOMATICALLY ASSESSING THE MENTAL STATE OF A USER VIA DRAWING PATTERN DETECTION AND MACHINE LEARNING

(71) Applicant: International Business Machines Corporation, Armonk, NY (US)

(72) Inventors: Jinho Hwang, Ossining, NY (US); Roxana Monge Nunez, San Jose (CR); Valentina Salapura, Chappaqua, NY (US); Maja Vukovic, New York, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/263,035

(22) Filed: Sep. 12, 2016

(51) Int. Cl.
| | |
|---|---|
| *G06K 9/00* | (2006.01) |
| *G06F 19/00* | (2018.01) |
| *G06N 5/04* | (2006.01) |
| *G06N 99/00* | (2010.01) |
| *G10L 25/63* | (2013.01) |

(52) U.S. Cl.
CPC .......... *G06F 19/345* (2013.01); *G06F 19/321* (2013.01); *G06K 9/00335* (2013.01); *G06K 9/00409* (2013.01); *G06K 9/00718* (2013.01); *G06N 5/047* (2013.01); *G06N 99/005* (2013.01); *G10L 25/63* (2013.01)

(58) Field of Classification Search
None
See application file for complete search history.

(56) References Cited

U.S. PATENT DOCUMENTS

| | | | | |
|---|---|---|---|---|
| 6,941,000 | B2* | 9/2005 | Wong | G06K 9/00476 |
| | | | | 382/113 |
| 9,445,767 | B2* | 9/2016 | Abreu | A61B 5/0002 |
| 2004/0210159 | A1* | 10/2004 | Kibar | A61B 5/4803 |
| | | | | 600/558 |

(Continued)

FOREIGN PATENT DOCUMENTS

WO     2010050767 A2     5/2010

OTHER PUBLICATIONS

MonDevices, A Smart Breathing Movement Monitor for Babies with Mobile App, May 16, 2008, https://monbaby.com/, pp. 1-5.

(Continued)

*Primary Examiner* — Nancy Bitar
(74) *Attorney, Agent, or Firm* — Scully, Scott, Murphy & Presser, PC; Yeen C. Tham, Esq.

(57) ABSTRACT

A method and system for automatically assessing the mental state of a user from a drawing made by the user. The mental state of the user is automatically assessed by digitizing a drawing and determining and analyzing drawing characteristics, including color, objects, and location. Video analytics are used to determine and analyze user time characteristics and mood characteristics. The mental state of the user is automatically determined by interpreting the color, object, location, time and mood characteristics and to automatically select a user action. A machine learning algorithm can learn developmental patterns of the user from historical data about a plurality of the user's drawings and the characteristics of the drawings to determine the mental state of the user. The machine learning algorithm can be used in selecting the user action.

21 Claims, 4 Drawing Sheets

(56) References Cited

U.S. PATENT DOCUMENTS

| | | | |
|---|---|---|---|
| 2005/0096555 A1* | 5/2005 | Elliott | A61B 5/02405 600/509 |
| 2006/0110203 A1* | 5/2006 | Grafton | G06F 3/01 400/489 |
| 2007/0288898 A1* | 12/2007 | Isberg | G06K 9/00335 717/124 |
| 2008/0253659 A1* | 10/2008 | Walch | G06K 9/00161 382/186 |
| 2009/0012819 A1* | 1/2009 | Mahesh | G06F 19/327 705/3 |
| 2009/0191525 A1* | 7/2009 | Shepherd | G09B 1/16 434/236 |
| 2011/0304577 A1* | 12/2011 | Brown | G06F 3/03545 345/174 |
| 2012/0063654 A1* | 3/2012 | Kim | G06F 19/00 382/128 |
| 2014/0201126 A1* | 7/2014 | Zadeh | G06K 9/627 706/52 |
| 2014/0335491 A1* | 11/2014 | Behrmann | G06Q 10/00 434/238 |

OTHER PUBLICATIONS

Helen South, "Color-Doodle and Symbol Interpretation", Sep. 2005, http://drawsketch.about.com/cs/tipsandideas/p/doodle_color.htm, pp. 1.

Do2Learn, "Educational Resources for Special Needs", Feb. 2013, http://www.do2learn.com/organizationtools/EmotionsColorWheel/, pp. 1.

Philip Goodman, "Interpreting Children's Drawings", Dec. 2014, http://www.newkidscenter.com/Interpreting-Children's-Drawings.html, pp. 1-2.

* cited by examiner

AUTOMATICALLY ASSESSING THE MENTAL STATE OF A USER VIA DRAWING PATTERN DETECTION AND MACHINE LEARNING

BACKGROUND OF THE INVENTION

This disclosure is directed to a method and system for automatically assessing the mental state of a user via drawing pattern detection and machine learning.

People, especially children, communicate and express themselves by drawing, so this becomes an important input to understand what the person thinks or feels at the moment. The drawings by children change over time, for example, they become more realistic as soon as the child becomes older. Many elderly use painting as their hobby and express their state of mind through drawings. Analysis of drawings for children is a developing field. Some examples of emotions and user states can be found at http://www.newkidscenter.com/Interpreting-Children's-Drawings.html).

There is a need to determine the mental state of a person. The mental state is important to understand the person's personality characteristics. The mental state, such as anger, anxiety, depression, etc., and historical data such as abuse, loss of loved person are important in the detection of mental problems. Such knowledge is also important in making a determination of whether corrective action, such as therapy, is advised, and if so, the type of recommended therapy.

SUMMARY OF THE INVENTION

One embodiment of this invention is directed to a computer implemented method for automatically assessing the mental state of a user from a drawing made by the user. In one embodiment, the mental state of the user is automatically assessed by digitizing a drawing and determining drawing characteristics, which can include color(s), object(s), and location. The method can further include analyzing the characteristics. The method can also include performing a video analysis of the user while making the drawing to determine user characteristics, the user characteristics including time characteristics and mood characteristics, analyzing the time characteristics and analyzing the mood characteristics. The method further includes automatically interpreting the color, object, location, time and mood characteristics to determine a mental state of the user and selecting a user action based on the determined the mental state of the user.

In one embodiment, a computer implemented method further includes creating a profile of the user and determining normal or abnormal patterns based on the profile to determine mental state of the user. In another embodiment, the computer implemented method includes determining developmental patterns of the user from historical data about a plurality of the user's drawings and the characteristics of the plurality of the user's drawings using a machine learning algorithm to facilitate a determination of the mental state of the user. By way of further example, the machine learning algorithm can use the determined the mental state of the user in the selection of a user action.

Another embodiment is directed to a system having at least one data processor connected to at least one memory that stores computer-readable program instructions, where execution of the computer-readable program instructions by the at least one data processor causes the system to automatically assess the mental state of a user from a drawing made by the user. In one embodiment, the mental state of the user is automatically assessed by digitizing a drawing and determining drawing characteristics, which can include color, objects, and location. The system can further include a drawing analyzer for analyzing the drawing characteristics. In some embodiments, the system also performs a video analysis of the user to determine and analyze user characteristics, such as time and mood. In some embodiments, the system automatically interprets drawing color(s), object(s), location, time and mood characteristics to determine a mental state of the user and selects a user action based on the determined the mental state of the user.

Another embodiment is directed to a computer program product having computer-readable program instructions on a non-transitory computer-readable medium, where execution of the computer-readable program instructions using a computer causes the computer to automatically assess the mental state of a user from a drawing made by the user by digitizing a drawing and determining drawing characteristics, the drawing characteristics including color, objects, and location; analyzing the color characteristics; analyzing the object characteristics; and analyzing the location characteristics. The computer program product can also include instructions for performing a video analysis of the user to determine user characteristics, the user characteristics including time characteristics and mood characteristics; analyzing the time characteristics; and analyzing the mood characteristics. The computer program product may further includes instructions for automatically interpreting the color, object, location, time and mood characteristics to determine the mental state of the user; and selecting a user action based on the determined mental state of the user.

DETAILED DESCRIPTION OF PREFERRED EMBODIMENTS

This disclosure is directed to a system and a method for automatically assessing the mental state of a user based on the drawing patterns and selecting an ameliorating action such as therapeutic treatment. The treatment for example may help with the user's recovery process from trauma, personal troubles at home and other circumstances that may affect the user's mental state.

Figure 1:
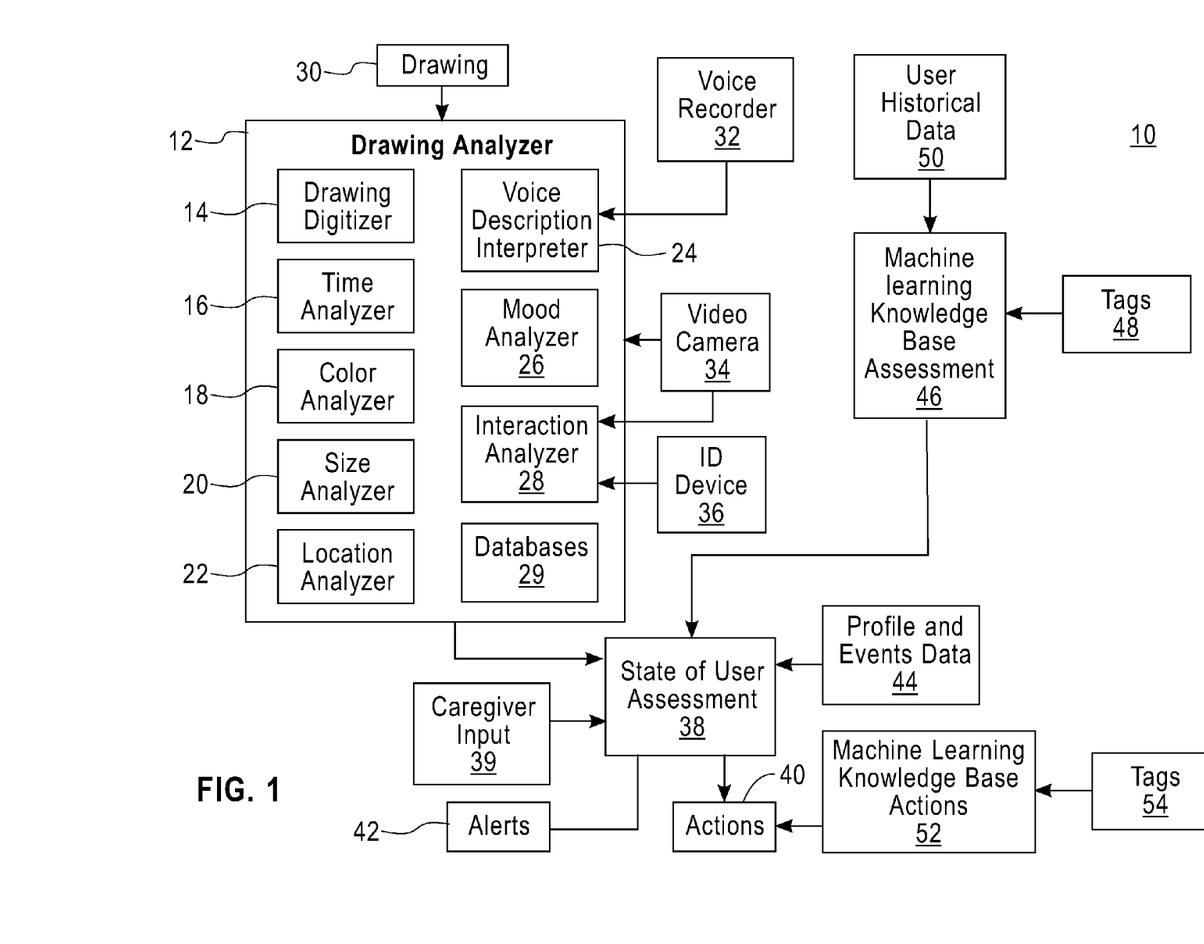
FIG. 1 is a block diagram of an exemplary system of automatically assessing the mental state of a user based on drawing patterns and selecting an ameliorating action according to one embodiment of the present disclosure.

FIG. 1 is a block diagram of a system of automatically assessing the mental state of a user based on drawing patterns and selecting an ameliorating action according to one embodiment of the present disclosure. FIG. 1 is a more detailed example of the program module 102 of FIG. 4 to be described later. The components of the system 10 include a drawing analyzer 12. The analyzer 12 includes one or more modules for performing various functions. These modules include a drawing digitizer 14, time analyzer 16, color analyzer 18, size analyzer 20, location analyzer 22, voice description analyzer 24, mood analyzer 26 and interaction analyzer 28. A drawing 30 is scanned and input into the drawing analyzer 12 for analysis.

The drawing analyzer 12 infers drawing patterns by analyzing drawing characteristics determined using drawing digitizer 14, time analyzer 16, color analyzer 18, size analyzer 20 and location analyzer 22. The drawing digitizer 14 performs analytics to determine visual characteristics of the drawing. The characteristics include data relating to color, objects, location, placement and composition, lines, marks, weight, style, people, faces, flowers, florals, geometric shapes, random abstract shapes, houses, windows, 3D boxes, ladders, arrows, walls, stars and hearts. The time analyzer 16 considers how much time the user needed to complete the drawing and other time related characteristics input to the drawing analyzer 12. An added benefit of the method and system of this disclosure is in the ability detect potential issues with the user over an extended period, by observing drawing styles over time, such as months and years. The color analyzer 18 considers number of colors used, the most dominant colors and other color characteristics. The size analyzer 20 considers the objects presented, the position on the paper, the relative size of the objects to each other and other size related characteristics. The location analyzer 22 considers the relative grouping of objects to each other, the location being depicted by the drawing and other location related characteristics.

Figure 2:
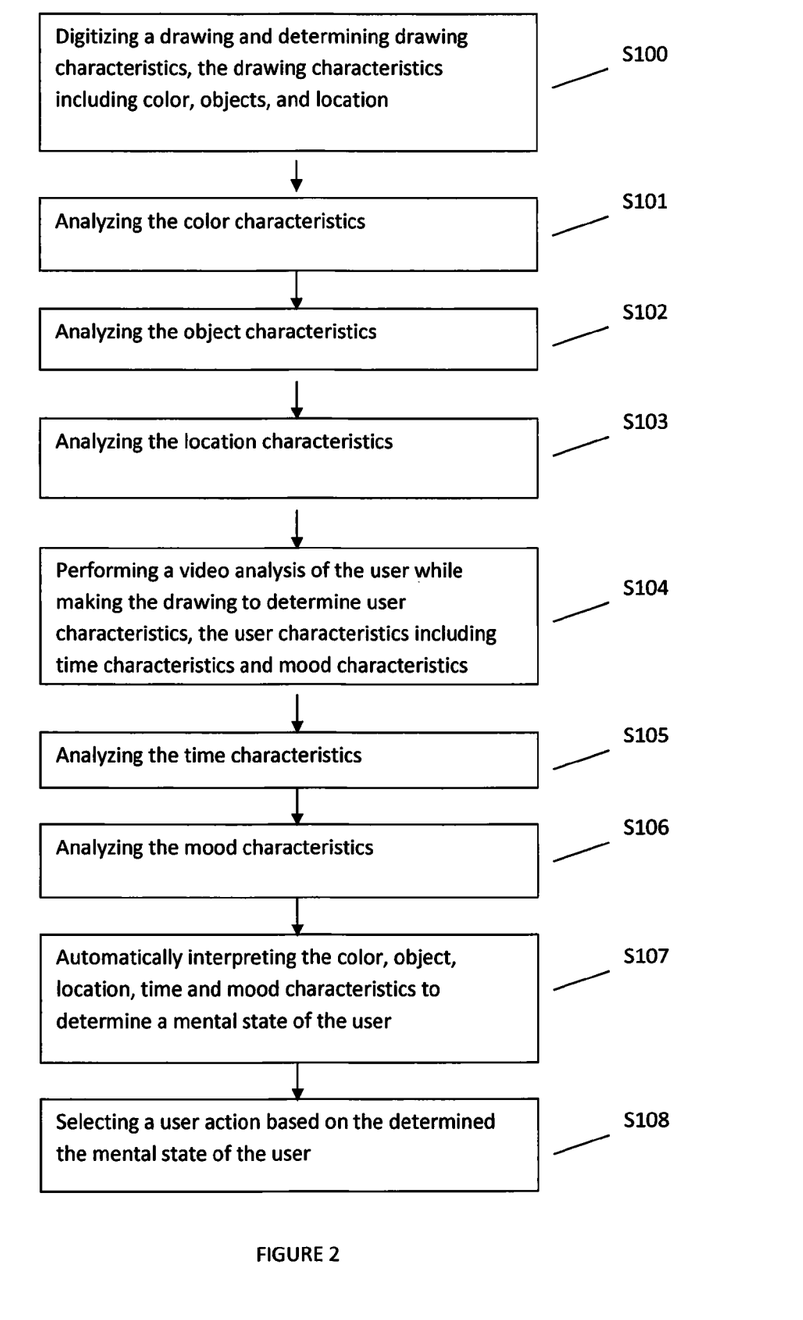
FIG. 2 is flow diagram of one embodiment of the method of automatically assessing the mental state of a user from a drawing.

The system of FIG. 1 performs a computer implemented method for automatically assessing the mental state of a user from a drawing made by the user. The method includes step S100 digitizing a drawing and determining drawing characteristics, the drawing characteristics including color, objects, and location; step S101 analyzing the color characteristics; step 102 analyzing the object characteristics; and step S103 analyzing the location characteristics. The method also includes step S104 performing a video analysis of the user while making the drawing to determine user characteristics, the user characteristics including time characteristics and mood characteristics; step S105 analyzing the time characteristics; and step S106 analyzing the mood characteristics. The method further includes step S107 automatically interpreting the color, object, location, time and mood characteristics to determine the mental state of the user; and step S108 selecting a user action based on the determined mental state of the user.

Figure 3:
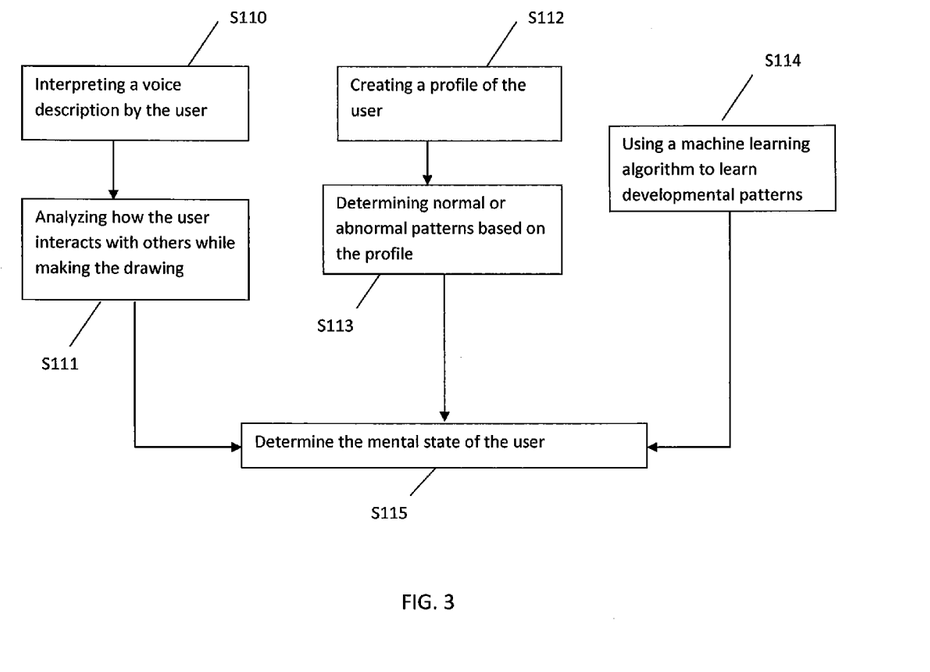
FIG. 3 is a flow diagram of further embodiments of the method of automatically assessing the mental state of a user from a drawing

In one embodiment, the system and method may also interpret the voice description by the user of the drawing. The meaning of a drawing becomes more accurate when the user is asked to explain what the drawing means. The system has a speaker or other voice recorder 32 that requests the user to explain what is being drawn or what was drawn. The drawing characteristics and the user's clarifications are analyzed by the voice description analyzer 24 to provide the assessment and actions accordingly. As shown in FIG. 3, the method includes step S110 interpreting a user voice description of the drawing and step S111 analyzing how the user interacts with others while making the drawing. The analysis of the user interaction with others is combined in step S115 with the step S107 in determining the mental state of the user.

In one embodiment, system has a video camera 34 that provides inputs regarding user's mood. The mood analyzer 26 analyzes those inputs for determining such as aspects as low self-esteem, fears, anxiety, low imagination, creativity, passion, love and other emotional states of the user.

In cases where more than one person is drawing, the video camera 34 provides input to interaction analyzer 14 for analyzing how each person reacts and draws by interacting with others. The parents or caregivers may optionally set up an identification device 36 such as little chip in their clothing or other device to identify the user and the user's drawings.

In one embodiment, a database module 29 contains various commercially available psychology databases for inferring drawing patterns. The module 29 may also include a categorical database to diagnose the mental state of drawers.

The state of user assessment module 38 takes in all the inputs from the drawing analyzer 12 and in some cases caregiver input 39, and automatically determines the mental state of the user. The assessment module 38 may illustrate the different mental states with different parameter values.

The module 38 will also automatically select a corrective, therapeutic and/or enhancing action and output the selected action at 40. The mental state may indicate a need for a corrective action, such as, therapy and the type of the recommended therapy. The actions may include soothing the user by using ambient music, recommending relocating the user due to, for example, undesired people around or an unsuitable room or area. The assessment module 38 may also provide an alert or warning 42 to a caregiver or parent that system is recommending an action based on the mental state of the user.

The mental state or states detected may, for example, include anger, anxiety, abuse, loss of loved person, depression and others states. The mental state detected may be the personality characteristics of the user.

In one embodiment, the method and system interprets the following personality characteristics from the associated drawing characteristics:

Impulsive child: Big figures, no necks, and asymmetry of limbs.

Anxious child: Clouds, rain, flying birds, no eyes on the figures

Shy child: Short figures, no nose or mouth, tiny figures and arms close to the body Angry child: Big hands and teeth, long arms, crossed eyes Insecure child: Monstrous figures, tiny heads, no hands, and slanted figures In one embodiment a profile and events data module 44 is used to create a profile for the user which may include data such as age, gender, and other related personal data. In addition, the profile may include data on events and any other relevant situations that are happening currently that are affecting the person, such as divorce, new school or job and other events. The data input from module 44 will allow the state of user assessment module 38 to compare the drawing analyzer data with the user information in determining normal or abnormal patterns and other affects on the user mental state. As shown in FIG. 3, the method includes step S112 creating a profile of the user and and step S113 determining normal or abnormal patterns based on the profile. The normal or abnormal patterns are combined in step S115 with the step S107 in determining the mental state of the user.

In one embodiment, the color analyzer 18 relies on visual associations of the colors in the drawing in the mental state assessment, such as, sky blue, green plants, red blood, brown earth, yellow sun. Colors also have a 'temperature'. Red, orange and yellow are warm colors, while green, blue, blue-grey and violet are cool. Examples of such associations and related meanings are found at: (http://drawsketch.about.com/cs/tipsandideas/p/doodle_color.htm).

In one embodiment, the meaning of certain colors is adaptable depending on the circumstances of the user and the user's profile input from module 44. For example, red often represents power. However, red can indicate anger ('seeing red') or a need to impose authority, but red is also a seasonal, festive color associated with holly berries and Santa Claus. Looking at red increases the heart rate. In China, red is the color of prosperity and joy.

Blue, black and gray are conventional colors, indicating stability and strength. Dark blue is often chosen as a corporate color in the financial sector to indicate security. Sea-green and blue can also have connotations of water and the ocean. Gray is sometimes called 'the color of sorrow'. In some cultures black is the color of the life-giving earth, while in western culture it is usually associated with darkness.

Purple may represent sexual frustration or a need to appear unorthodox, and is a favorite color of artists. Historically, purple has represented royalty, and in darker hues suggests magic and mystery. Brown can suggest the earth and autumn. A preference for brown can indicate a conservative personality, even repression. Of course, in clothing and furnishings that depends on fashion, though trends can indicate the mood of the times. Green usually regarded as a restful color suggesting well-being, and is favored by well-balanced individuals. This is at odds with some associations, 'green with envy', 'going green' with nausea, and money (due to the 'greenback').

In one embodiment, the color analyzer 18 looks for the right emotion from the drawing through the emotional color wheel, one example of which is found at: (http://www.do2learn.com/organizationtools/EmotionsColorWheel/).

In one embodiment historical data 50 about the drawings and the context of the drawings is input to a machine learning module 46 to enable learning about the user's development patterns. Care giver or user tags 48 may be input for the drawing. The state of assessment module 38 extracts patterns of behavior from the machine learning data and determines the mental state of the user based on the drawing analysis trained through historical data with correct tags. As shown in FIG. 3, the method includes step S114 using a machine learning algorithm to learn developmental patterns. The developmental patterns are combined in step S115 with the step S107 in determining the mental state of the user.

In one embodiment, a machine learning module 52 uses a machine learning algorithm to learn what actions are best for different classes of users so that other users can benefit as the system learns. Tags 54 may be added for a recommended action when the user likes it. The machine learning module 52 enables the state of user assessment module to determine with a certain level of confidence that a particular action is the correct action for the user.

In one embodiment, categories of the assessment analysis include various states of mind and drawing types. In addition, the output can be multiple with different probabilities. The analysis categories may include:

Emotions: Deal with emotions like anger and sadness through these helpful exercises.

Relaxation: Level of stress or relaxation.

Happiness: how much drawers appreciate and focus on the good. This is all about reflecting on personal happiness.

Portraits: a great way to get to know self and relationships with others is through portraits.

Trauma and Loss: This will ask one to face some unpleasant aspects of life, but with the goal of overcoming them.

Collaging: a different way of drawing based on preferences.

Self: Examine aspects if who one is and how one sees the world through drawings.

Gratitude: that will help one be happy about what one has and expresses his/her gratitude for something.

Inside the Mind: Take a look inside mind to see what's going on.

The method and system of analyzing drawing patterns as disclosed herein serves several the purposes, including but not limited to:

Identification/Referral: To identify children who need special education and related services;

Eligibility: To determine whether a child is a "child with a disability" under the Individuals with Disabilities Education Act (IDEA) definition;

Planning an Individualized Education Program (IEP) for children ages 3-22: To develop goals and plan service delivery;

Planning an Individualized Family Service Plan (IFSP) for children ages birth-2: To identify the major results or outcomes expected to be achieved for the child and family;

Instructional strategies: To determine ways to help a child learn; and

Measuring progress: To provide a present level of performance for measuring a child's progress.

Figure 4:
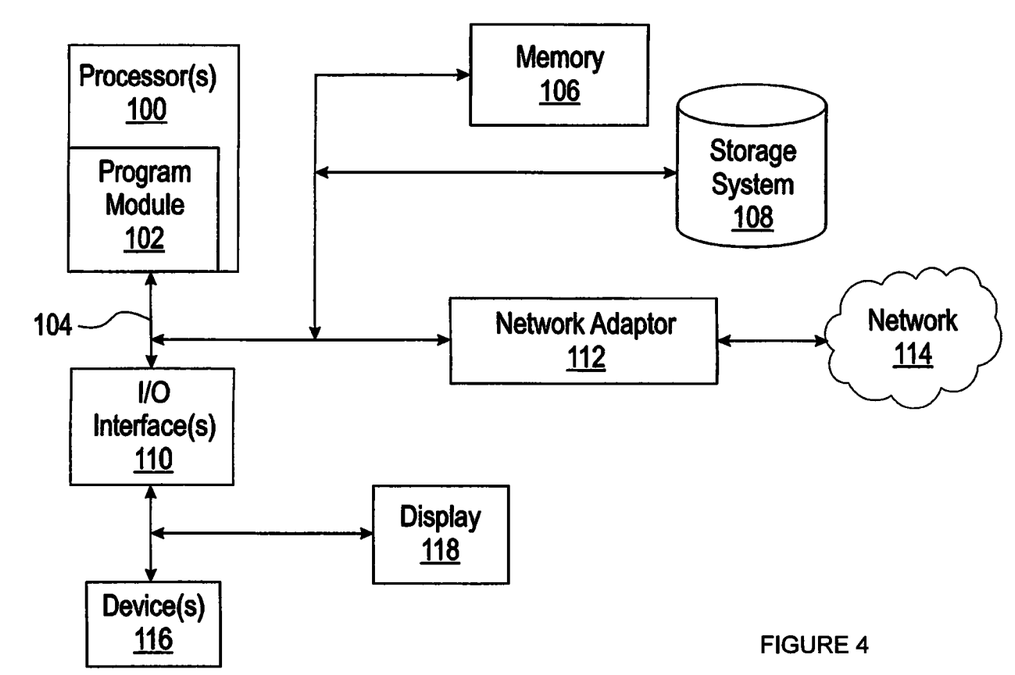
FIG. 4 is a block diagram of an exemplary computing system suitable for implementation of the embodiments of the invention disclosed in this specification.

FIG. 4 illustrates a schematic of an example computer or processing system that may implement the method and system for assessing the mental state of a user via drawing pattern detection and machine learning in one embodiment of the present disclosure. The computer system is only one example of a suitable processing system and is not intended to suggest any limitation as to the scope of use or functionality of embodiments of the methodology described herein. The processing system shown may be operational with numerous other general purpose or special purpose computing system environments or configurations. Examples of well-known computing systems, environments, and/or configurations that may be suitable for use with the processing system shown in FIG. 4 may include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The computer system may be described in the general context of computer system executable instructions, such as program modules, being executed by a computer system. Generally, program modules may include routines, programs, objects, components, logic, data structures, and so on that perform particular tasks or implement particular abstract data types. The computer system may be practiced in distributed cloud computing environments where tasks are performed by remote processing devices that are linked through a communications network. In a distributed cloud computing environment, program modules may be located in both local and remote computer system storage media including memory storage devices.

The components of computer system may include, but are not limited to, one or more processors or processing units 100, a system memory 106, and a bus 104 that couples various system components including system memory 106 to processor 100. The processor 100 may include a program module 102 that performs the methods described herein. The module 102 may be programmed into the integrated circuits of the processor 100, or loaded from memory 106, storage device 108, or network 114 or combinations thereof.

Bus 104 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system may include a variety of computer system readable media. Such media may be any available media that is accessible by computer system, and it may include both volatile and non-volatile media, removable and non-removable media.

System memory 106 can include computer system readable media in the form of volatile memory, such as random access memory (RAM) and/or cache memory or others. Computer system may further include other removable/non-removable, volatile/non-volatile computer system storage media. By way of example only, storage system 108 can be provided for reading from and writing to a non-removable, non-volatile magnetic media (e.g., a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 104 by one or more data media interfaces.

Computer system may also communicate with one or more external devices 116 such as a keyboard, a pointing device, a display 118, etc.; one or more devices that enable a user to interact with computer system; and/or any devices (e.g., network card, modem, etc.) that enable computer system to communicate with one or more other computing devices. Such communication can occur via Input/Output (I/O) interfaces 110.

Still yet, computer system can communicate with one or more networks 114 such as a local area network (LAN), a general wide area network (WAN), and/or a public network (e.g., the Internet) via network adapter 112. As depicted, network adapter 112 communicates with the other components of computer system via bus 104. It should be understood that although not shown, other hardware and/or software components could be used in conjunction with computer system. Examples include, but are not limited to: microcode, device drivers, redundant processing units, external disk drive arrays, RAID systems, tape drives, and data archival storage systems, etc.

The present invention may be a system, a method, and/or a computer program product at any possible technical detail level of integration. The computer program product may include a non-transitory computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements, if any, in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

In addition, while preferred embodiments of the present invention have been described using specific terms, such description is for illustrative purposes only, and it is to be understood that changes and variations may be made without departing from the spirit or scope of the following claims.

What is claimed is:

1. A computer implemented method for automatically assessing the mental state of a user from a drawing made by the user comprising:

digitizing a drawing and determining drawing characteristics, the drawing characteristics including color, objects, and location;

analyzing the color characteristics;

analyzing the object characteristics;

analyzing the location characteristics;

performing a video analysis of the user while making the drawing to determine user characteristics, the user characteristics including time characteristics and mood characteristics;

requesting the user to provide a voice description of the drawing;

performing an audio analysis of the user's voice description of the drawing;

analyzing the time characteristics;

analyzing the mood characteristics;

receiving a profile of the user including personal user data and user events data;

automatically interpreting the color, object and location characteristics of the drawing, the user's voice description of the drawing, and the time and mood characteristics of the user to obtain drawing analysis data;

automatically comparing the drawing analysis data with the profile and determining developmental patterns based on the comparison;

accessing historical data about a plurality of the user's drawings, the historical data including drawing characteristics of the plurality of the user's drawings, video analysis of the user while making the plurality of drawing and audio analysis of the user's voice description of the plurality of drawings;

inputting the historical data into a machine learning algorithm computer program module having a machine learning algorithm;

inputting drawing tags into the machine learning algorithm computer program module, the drawing tags being at least one of care giver tags and user tags;

training the machine learning algorithm based on the historical data and the drawing tags to learn developmental patterns of the user;

combining the developmental patterns of the user learned from the machine learning algorithm and the developmental patterns of the user determined from the comparison of the drawing analysis data with the profile, to determine the mental state of the user over time; and selecting a user action based on the mental state of the user determined over time.

2. The computer implemented method of claim 1 further comprising analyzing how the user interacts with others while making the drawing.

3. The computer implemented method of claim 1 further comprising using one or more psychology databases for inferring drawing patterns.

4. The computer implemented method of claim 1 further comprising providing an alert of the selection of an action, based on the determined mental state of the user.

5. The computer implemented method of claim 1 further comprising adapting the interpretation of color based on the profile.

6. The method of claim 1, wherein the machine learning algorithm is used in selecting the user action based on the determined the mental state of the user.

7. A system comprising:
   at least one data processor connected to at least one memory that stores software instructions, where execution of the software instructions by the at least one data processor causes the system to automatically assess the mental state of a user from a drawing made by:
   digitizing a drawing and determining drawing characteristics, the drawing characteristics including color, objects, and location;
   analyzing the color characteristics;
   analyzing the object characteristics;
   analyzing the location characteristics;
   performing a video analysis of the user while making the drawing to determine user characteristics, the user characteristics including time characteristics and mood characteristics;
   requesting the user to provide a description of the drawing;
   performing an audio analysis of the user's voice description of the drawing;
   analyzing the time characteristics;
   analyzing the mood characteristics;
   receiving a profile of the user including personal user data and user events data;
   automatically interpreting the color, object and location characteristics of the drawing, the user's voice description of the drawing, and the time and mood characteristics of the user to obtain drawing analysis data;
   automatically comparing the drawing analysis data with the profile and determining developmental patterns based on the comparison;
   accessing historical data about a plurality of the user's drawings, the historical data including drawing characteristics of the plurality of the user's drawings, video analysis of the user while making the plurality of drawing and audio analysis of the user's voice description of the plurality of drawings;
   inputting the historical data into a machine learning algorithm computer program module having a machine learning algorithm;
   inputting drawing tags into the machine learning algorithm computer program module, the drawing tags being at least one of care giver tags and user tags;
   training the machine learning algorithm based on the historical data and the drawing tags to learn developmental patterns of the user;
   combining the developmental patterns of the user learned from the machine learning algorithm and the developmental patterns of the user determined from the comparison of the drawing analysis data with the profile, to determine the mental state of the user over time; and
   selecting a user action based on the determined the mental state of the user determined over time.

8. The system of claim 7 further including analyzing how the user interacts with others while making the drawing.

9. The system of claim 7 further including using one or more psychology database for inferring drawing patterns to determine the mental state of the user.

10. The system of claim 7 further including providing an alert of the selection of an action based on the determined mental state of the user.

11. The system of claim 7 further including creating a profile of the user and determining normal or abnormal patterns based on the profile to determine mental state of the user.

12. The system of claim 7 wherein the machine learning algorithm is used in selecting the user action based on the determined the mental state of the user.

13. A non-transitory computer readable medium storing a computer program product comprising: program instructions on a computer-readable storage medium, where execution of the program instructions using a computer causes the computer to automatically assess the mental state of a user from a drawing made by the user by: digitizing a drawing and determining drawing characteristics, the drawing characteristics including color, objects, and location; analyzing the color characteristics; analyzing the object characteristics; analyzing the location characteristics; performing a video analysis of the user while making the drawing to determine user characteristics, the user characteristics including time characteristics and mood characteristics; requesting the user to provide a voice description of the drawing: performing an audio analysis of the user's voice description of the drawing; analyzing the time characteristics; analyzing the mood characteristics; receiving a profile of the user including personal user data and user events data; automatically interpreting the color, object and location characteristics of the drawing, the user's voice description of the drawing, and the time and mood characteristics of the user to obtain drawing analysis data; automatically comparing the drawing analysis data with the profile and determining developmental patterns based on the comparison: accessing historical data about a plurality of the user's drawings, the historical data including drawing characteristics of the plurality of the user's drawings, video analysis of the user while making the plurality of drawing and audio analysis of the user's voice description of the plurality of drawings; inputting the historical data into a machine learning algorithm n computer program module having a machine learning algorithm; inputting drawing tags into the machine learning algorithm computer program module, the drawing tags being at least one of care giver tags and user tags; training the machine learning algorithm based on the historical data and the drawing tags to learn developmental patterns of the user combining the-developmental patterns of the user learned from the-machine learning algorithm and the developmental patterns of the user determined from the comparison of the drawing analysis data with the profile, to determine the mental state of the user over time; and selecting a user action based on the determined the mental state of the user determined over time.

14. The computer program product of claim 13 further including analyzing how the user interacts with others while making the drawing.

15. The computer program product of claim 13 further including creating a profile of the user and determining normal or abnormal patterns based on the profile to determine mental state of the user.

16. The computer implemented method of claim 1 wherein the machine learning algorithm learns what user actions are correct for different classes of users.

17. The computer implemented method of claim 16 wherein the machine learning algorithm determines that a particular user action is the correct action for the user with a level of confidence.

18. The system of claim 7 wherein the machine learning algorithm learns what user actions are correct for different classes of users.

19. The system of claim 17 wherein the machine learning algorithm determines that a particular user action is the correct action for the user with a level of confidence.

20. The computer program product of claim 13 wherein the machine learning algorithm learns what user actions are correct for different classes of users.

21. The computer program product of claim 20 wherein the machine learning algorithm determines that a particular user action is the correct action for the user with a level of confidence.

\* \* \* \* \*